United States Patent [19]

Chiang

[11] Patent Number: 5,070,199
[45] Date of Patent: Dec. 3, 1991

[54] PROCESS FOR THE PREPARATION OF 2-AMINO-4-METHYL-6-METHOXY-1,3,5-TRIAZINE

[75] Inventor: George C. Chiang, Wilmington, Del.

[73] Assignee: E. I. Du Pont de Nemours and Company, Wilmington, Del.

[21] Appl. No.: 703,528

[22] Filed: May 21, 1991

[51] Int. Cl.$^5$ .......................................... C07D 251/42
[52] U.S. Cl. .................................................. 544/194
[58] Field of Search ........................................ 544/194

[56] References Cited

U.S. PATENT DOCUMENTS 4,886,881 12/1989 Chiang et al. ........................ 544/194

Primary Examiner—John M. Ford
Attorney, Agent, or Firm—James A. Costello

[57] ABSTRACT

A process for preparing 2-amino-4-methyl-6-methoxy-1,3,5-triazine by reacting dialkyl-N-cyanoimidocarbonate with acetamidine hydrochloride or an O-alkylacetamidate hydrochloride under basic conditions.

14 Claims, No Drawings

PROCESS FOR THE PREPARATION OF 2-AMINO-4-METHYL-6-METHOXY-1,3,5-TRIAZINE

FIELD OF THE INVENTION

This invention is directed to a one-step process for the preparation of 2-amino-4-methyl-6-methoxy-1,3,5-triazine, an intermediate in the manufacture of sulfonylurea herbicides.

STATE OF THE ART

U.S. Pat. Nos. 4,169,719; 4,394,506; 4,886,881 and 4,993,450 disclose the preparation of 2-aminotriazines.

DD 252374 discloses the use of cyanoguanidine in the presence of Cu(OAc)$_2$ for the preparation of 2-aminotriazone.

*Journal of Organic Chemistry*, 28, 1816 (1963) discloses the preparation of 2-aminotriazines from N-cyanoimino esters and methylisourea.

*Helv. Chim. Acta.*, 33, 1365 (1950) also disclose the preparation of 2-aminotriazines via cyanuric chloride and a Grignard reagent.

SUMMARY OF THE INVENTION

This invention pertains to a process for preparing 2-amino-4-methyl-6-methoxy-1,3,5-triazine in good yield by reacting acetamidine hydrochloride or an O-alkylacetamidate hydrochloride with dialkyl-N-cyanoimidocarbonate in a solvent containing a base. The N-cyanoimidocarbonate can be added to the reaction before or after neutralization of the hydrochloride salt(s). The ingredients can be combined in any order in a convenient one-step, one-pot process.

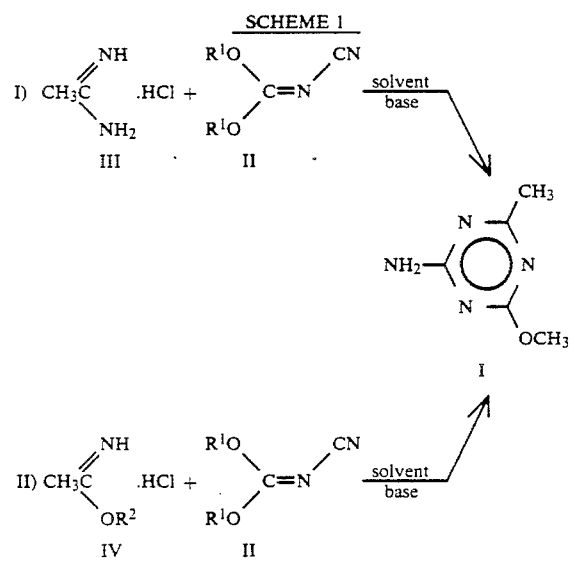

wherein:
R$^1$ and R$^2$ are independently C$_1$–C$_3$ alkyl. The C$_1$–C$_3$ alkyl includes methyl, ethyl, propyl and isopropyl moieties.

The reaction conditions for Equations I and II are as follows. Useful solvents include water, methanol, acetonitrile and toluene. Methanol is preferred. Reaction temperatures are typically 0° C. to 120° C. with 0° C. to 65° C. being preferred. Bases include triethylamine, sodium hydroxide, sodium methoxide, potassium hydroxide and potassium methoxide. Preferred are sodium hydroxide, sodium methoxide and potassium hydroxide. Reaction times are about 0.5 to 4 hours, most usually 1 to 3 hours.

DETAILS OF THE INVENTION

The process of Equation 1 can be carried out by combining ingredients in any order. Typically, it is carried out by treating acetamidine hydrochloride in a solvent, such a methanol, cooled to approximately 10° C., with an equimolar amount of a base, such as sodium or potassium methoxide. Following this neutralization to liberate free acetamidine, dialkyl-N-cyanoimidocarbonate is added and the mixture is stirred for 1 to 2 hours. The mixture can be heated and refluxed briefly to shorten the overall reaction time. When the solvent is toluene, the product triazine is conveniently isolated by cooling the reaction mixture to room temperature, if necessary, and isolating the triazine from the reaction mixture by washing with water and drying, followed by evaporation. When methanol or acetonitrile is the solvent, the reaction mixture is poured into ice water and the product filtered or isolated by conventional techniques, such as extraction with an organic solvent. Similarly, when water is the solvent, the triazine product is filtered or isolated by extraction.

The process of Equation II can be carried out in an analogous fashion, replacing acetamidine hydrochloride with an O-alkylacetamidate hydrochloride. Alternatively, dialkyl-N-cyanoimidocarbonate can be reacted with acetamidine, the reaction product of acetamidine hydrochloride and base, or with O-alkylacetamidate, the reaction product of O-ethylacetamidate hydrochloride and base. This alternative reaction can be conducted with sodium methoxide as the base and methanol as solvent under ice bath cooling. The mixture then is heated and refluxed. After cooling in an ice bath, the solids are filtered off, washed and dried to yield the subject triazine.

Acetamidine hydrochloride and o-alkylacetamidate hydrochlorides are commercially available. Alternatively, these reagents can be prepared in-situ. Amidines can be prepared by reaction of imidates with ammonia. Excellent reviews are Chem. Rev. 35, 351 (1944) and 61, 179 (1961). Acetonitrile is readily converted to imidate salts by reacting with HCl gas in lower alcohols. Subsequent addition of ammonia gas readily converts the imidate salts to acetamidine salts in good yields. Upon addition of bases (NaOMe, NaOH, or KOH). Acetamidine becomes free and readily reacts with dimethyl N-cyanoimidocarbonate to form 2-amino-4-methyl-6-methoxy-1,3,5-triazine in excellent yields. Dimethyl N-cyanoimidocarbonate is known and easily prepared. See, for example, J. Heterocyclic Chem., 21, 61–4 (1984), DE 3,225,249 and EP 14064.

The following Examples further illustrate the invention.

EXAMPLE 1

A solution of 25% sodium methoxide (22 g) was charged dropwise to a solution of 40 mL of methanol and 9.5 g of acetamidine hydrochloride at 10° C. Upon complete addition, it was stirred at 10° C. for 15 minutes. Then, 11.4 g of dimethyl N-cyanoimidocarbonate (from SKW Trostberg) was charged and an exotherm of 15° C. was observed. The reaction mixture was stirred at 25° C. for one hour and then heated to reflux for 15 minutes. It was cooled to 20° C., poured onto 200 mL of ice water and filtered. The crystals were washed with water, methanol and ether. After drying overnight in an oven at 70° C., the product weighed 13.0 g (92.8% yield). It was identified to be pure 2-methyl-4-amino-6-methoxy-1,3,5-triazine by comparing with authentic samples.

EXAMPLE 2

Acetamidine hydrochloride (9.5 g) was added to a predissolved solution of methanol (50 mL) and KOH pellets (6.8 g) at 10° C. It was then dropped into a solution of 11.4 g of dimethyl N-cyanoimidocarbonate and 40 mL of methanol at 10° C. After the addition, the reaction mixture was stirred at 25° C. for 2 hours onto 40 mL of ice water. The solid crystals were collected by filtering and washing with water and methanol. After drying at 70° C. overnight, 11.8 g (84% yield) of 2-methyl-4-amino-6-methoxy-1,3,5-triazine was obtained.

EXAMPLE 3

In a 100 mL flask was placed 7 g of o-ethylacetamidate hydrochloride, 6.4 g of dimethyl N-cyanoimidocarbonate (SKW) and 30 mL of methanol. It was kept in an ice bath and 35 g of 25% sodium methoxide was charged dropwise over a 15 minute period. A thick white slurry was formed. It was heated to reflux for 3 hours and then cooled in ice bath. The solids were filtered, washed with water and methanol. After drying at 70° C. overnight, 3.4 g of the title compound was obtained. The yield was 43%.

What is claimed is:

1. A method for making 2-amino-4-methyl-6-methoxy-1,3,5-triazine comprising reacting dialkyl-N-cyanoimidocarbonate of the formula

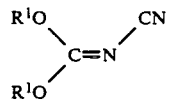

wherein $R^1$ is $C_1$–$C_3$ alkyl with acetamidine hydrochloride or an O-alkylacetamidate hydrochloride under basic conditions.

2. A method according to claim 1 wherein dialkyl-N-cyanoimidocarbonate is reacted with acetamidine hydrochloride.

3. A method according to claim 1 wherein dialkyl-N-cyanoimidocarbonate is reacted with an O-alkylacetamidate hydrochloride.

4. A method according to claim 1 comprising reacting the ingredients in the presence of an aqueous or organic solvent and an organic or inorganic base.

5. A method according to claim 1 wherein the solvent is selected from the group water, methanol, acetonitrile and toluene and the base is selected from the group triethylamine, sodium hydroxide, sodium methoxide and potassium hydroxide.

6. A method according to claim 5 wherein the solvent is methanol and the base is selected from the group sodium hydroxide, potassium hydroxide and sodium methoxide.

7. A method according to claim 2 comprising reacting the ingredients in the presence of an aqueous or organic solvent and an organic or inorganic base.

8. A method according to claim 7 wherein the solvent is selected from the group water, methanol, acetonitrile and toluene and the base is selected from the group triethylamine, sodium hydroxide, sodium methoxide and potassium hydroxide.

9. A method according to claim 8 wherein the solvent is methanol and the base is selected from the group sodium hydroxide, potassium hydroxide and sodium methoxide.

10. A method according to claim 3 comprising reacting the ingredients in the presence of an aqueous or organic solvent and an organic or inorganic base.

11. A method according to claim 10 wherein the solvent is selected from the group water, methanol, acetonitrile and toluene and the base is selected from the group triethylamine, sodium hydroxide, sodium methoxide and potassium hydroxide.

12. A method according to claim 11 wherein the solvent is methanol and the base is selected from the group sodium hydroxide, potassium hydroxide and sodium methoxide.

13. A method according to claim 2 comprising reacting dialkyl-N-cyanoimidocarbonate with acetamidine, the reaction product of acetamidine hydrochloride and base.

14. A method according to claim 3 comprising reacting dialkyl-N-cyanoimidocarbonate with an O-alkylacetamidate, the reaction product of an O-alkylacetamidate hydrochloride and base.

* * * * *